United States Patent [19]

Konings et al.

[11] Patent Number: 5,376,632
[45] Date of Patent: Dec. 27, 1994

[54] CYCLODEXTRIN BASED ERYTHROPOIETIN FORMULATION

[76] Inventors: Frank J. Konings, Leeuwerikendreef 1, B-2970-Schilde; Marcus J. M. Noppe, Pater Antonissenstraat 14, B-2920-Kalmthout; Jean L. Mesens, Moereind 17, B-2275-Wechelderzande, all of Belgium

[21] Appl. No.: 906,780

[22] Filed: Jun. 30, 1992

[51] Int. Cl.$^5$ ............... A61K 37/10; C08B 37/16
[52] U.S. Cl. .................................. 514/8; 514/21; 514/58; 514/777; 514/814; 530/380; 530/395; 530/397; 536/46; 536/103
[58] Field of Search ............... 514/8, 21, 58, 777, 514/814; 530/380, 395, 397; 536/46, 103

[56] References Cited

U.S. PATENT DOCUMENTS

| | | | |
|---|---|---|---|
| 4,806,524 | 2/1989 | Kawaguchi et al. | 514/8 |
| 4,824,938 | 4/1989 | Koyama et al. | 514/8 |
| 5,024,998 | 6/1991 | Bodor | 514/58 |
| 5,068,227 | 11/1991 | Weinshenker | 514/58 |

FOREIGN PATENT DOCUMENTS

| | | | |
|---|---|---|---|
| 178576 | 4/1986 | European Pat. Off. | A61K 37/24 |
| 178665 | 4/1986 | European Pat. Off. | A61K 37/24 |
| 308181 | 12/1987 | European Pat. Off. | A61K 47/00 |
| 2160528 | 12/1985 | United Kingdom | C07K 3/00 |
| 2189245 | 10/1987 | United Kingdom | C07D 309/02 |
| WO90/03784 | 4/1990 | WIPO | A61K 9/18 |

OTHER PUBLICATIONS

Müller et al, *Journal of Pharmaceutical Sciences*, vol. 75, No. 6, pp. 571–572, Jun. 1986.

*Primary Examiner*—Michael G. Wityshyn
*Assistant Examiner*—Abdel A. Mohamed
*Attorney, Agent, or Firm*—Charles J. Metz

[57] ABSTRACT

The present invention relates to a new pharmaceutical composition for parenteral and local administration comprising an aqueous solution of erythropoietin and a β- or γ-cyclodextrin hydroxyalkyl derivative. The invention also relates to novel lyophilized or spray-dried erythropoietin compositions comprising a β- or γ-cyclodextrin hydroxyalkyl derivative, to processes for preparing such aqueous, lyophilized or spray-dried compositions and to a method for simultaneously stabilizing erythropoietin in an aqueous solution and preventing it from being adsorbed to surfaces.

4 Claims, No Drawings

CYCLODEXTRIN BASED ERYTHROPOIETIN FORMULATION

The present invention relates to a new pharmaceutical composition for parenteral and local administration comprising an aqueous solution of erythropoietin and a β- or γ-cyclodextrin hydroxyalkyl derivative. The invention also relates to novel lyophilized or spray-dried erythropoietin compositions comprising a β- or γ-cyclodextrin hydroxyalkyl derivative, to processes for preparing such aqueous, lyophilized or spray-dried compositions and to a method for simultaneously stabilizing erythropoietin in an aqueous solution and preventing it from being adsorbed to surfaces. More particularly the said new composition is particularly useful for the direct subcutaneous, nasal or ocular administration of erythropoietin for the treatment of anaemia. In a further aspect of the invention there is provided a novel method of treating mammals suffering from anaemia by administering locally to said mammals an effective erythropoietic mount of the instant compositions.

Erythropoietin is a circulating glycoprotein hormone which induces an increase in red cell mass, mainly by stimulating the erythroid marrow. The hormone is present in trace amounts and is primarily produced from still unidentified sites in the adult kidney and fetal liver cells.

It has been shown that the administration of a few micrograms of erythropoietin, in one or multiple doses, is effective in correcting the anaemia of end stage renal disease. This dosage level should however strictly be observed. A therapy with erythropoietin therefore requires a dosage form which enables an accurate administration of trace amounts of the exogenous hormone.

The production of erythropoietin by recombinant DNA technology and the subsequent demonstration that this new agent is as effective as the native hormone led to the study of its use in various therapeutic applications. Erythropoietin, however, has one significant drawback which hitherto hindered the development of a lot of therapeutic applications: it is not stable, particularly not in an aqueous solution. Even at very low temperatures ($-80°$ C.) a substantial decrease in activity can be observed.

This decrease in activity is on the one hand due to the degradation of erythropoietin in an aqueous solution. On the other hand the decrease in activity is the result of the substantial adsorption of erythropoietin on the inner surface of the wall of the syringe or container which, in turn, causes further degradation.

Under these circumstances various attempts have been made to develop a method for preventing erythropoietin in aqueous solution from being adsorbed on the inner surface of the wall of a container and for preventing it from degrading.

The EP-A-178576 teaches a method of preventing erythropoietin in an aqueous solution from being adsorbed on the inner surface of a glass or plastic container by addition of -inter alia- human serum albumin, bovine serum albumin, lecithin, dextrans, methylcellulose, polyethylene glycols, ethylene oxide-propylene oxide copolymer and/or polyoxyethylene hydrogenated castor oil. It was demonstrated that the recovery of erythropoietin in such a formulation totalled 75-98% after two hours at 20° C., whereas in the control formulation only 16% was recovered. It is Applicant's own experience however that one can not retain the long term functional stability of erythropoietin in such formulations. In order to obtain a long term functional stability not only the polypeptide structure but aim the carbohydrate structure of the glycoprotein should remain intact as it has been demonstrated that proper glycolysation and sialylation are essential for the hormone's function in vivo. In addition one may expect that the aforementioned formulations could elicit immunogenic reactions in certain subjects, especially after repeated injections. Blood derivatives such as human serum albumin may also be the source of life threatening viral infections.

In EP-A-178665 there are described stabilizers which are useful in freeze-dried and aqueous erythropoietin formulations. As stabilizing agents there are mentioned polyethylene glycols, proteins, sugars, ammo acids, inorganic salts, organic salts and sulfur-containing reducing agents. It was demonstrated that after one week the activity of erythropoietin in the stabilized formulations at 25° C. decreased to 67-73% of its original activity whereas the activity in the unstabilized formulation decreased to 46%. Also in this instance, it was found that the addition of the above stabilizers does not guarantee a long term functional stability of erythropoietin.

The EP-A-306824 describes stable freeze-dried erythropoietin formulations comprising urea and amino acids for stabilization and surfactants to prevent adsorption. As a major drawback it is admitted therein that the erythropoietin formulations reconstituted in aqueous form have a limited stability of some months at room temperature. Therefore the customer is practically obliged to reconstitute the freeze-dried formulation each time again just before administration.

In WO-90/03784 there is described a method for the solubilization and/or stabilisation of polypeptides, especially proteins, by means of derivatives of β- and γ-cyclodextrin, as well as compositions comprising a polypeptide and such cyclodextrin derivatives. In the extensive list of suitable proteins erythropoietin is mentioned but no specific example discloses a composition comprising erythropoietin. Among the suitable cyclodextrin derivatives there are mentioned β- and γ-cyclodextrins modified with -inter alia-hydroxypropyl or hydroxyethyl. The average number of alkoxy units per cyclodextrin ranges from about 4.7 to 7 for β-cyclodextrin (M.S.=0.67 to 1) and from about 7 to 8 for γ-cyclodextrin (M.S.=0.875 to 1). Particularly noteworthy is the low weight-by-weight ratio of cyclodextrin derivative to polypeptide, namely about 1:1 to about 200:1.

The aim of the present invention is to prepare an economical, practicable and safe erythropoietin formulation which allows self administration causing little discomfort and no local irritation. A prerequisite to obtain this goal is the preparation of an aqueous erythropoietin formulation in which the glycoprotein retains its functional stability over a long period of time. Such erythropoietin formulations preferably should be administered directly without any further manipulations such as reconstitution or dilution.

Surprisingly it has been found that the said precondition is fulfilled by the compositions described hereinafter.

The present invention relates to a pharmaceutical composition for parenteral or local administration comprising an aqueous solution of erythropoietin and β- or γ-cyclodextrin wherein one or more of the hydroxy moieties of the anhydroglucose units of the cyclodextrin have been replaced by a radical of formula

 (I), wherein Alk represents a straight or branched chain $C_{1-6}$alkanediyl radical wherein optionally one hydrogen atom of said radical Alk may be replaced by a hydroxy group; and "n" ranges from 1 to 5, in particular from 1 to 3 and more in particular is 1. The average number of alkoxy units per cyclodextrin, i.e. the average sum of "n" of all radicals of formula (I) substituted on the cyclodextrin can range from less than 1 to about 50, in particular from 1 to 20, more in particular from 1 to 10, or from 1 to 5.

Preferably the average number of alkoxy units per cyclodextrin ranges from 2 to 4, in particular from 2.5 to 3.5 and most particularly is about 2.8 in β-cyclodextrin derivatives and about 3.2 in γ-cyclodextrin derivatives.

In the foregoing definitions the term "$C_{1-6}$alkanediyl" defines bivalent straight or branched chain hydrocarbon radicals containing from 1 to 6 carbon atoms such as, for example, 1,2-ethanediyl, 1,2-propanediyl, 1,3-propanediyl, 1,4-butanediyl, 1,5-pentanediyl, 1,6-hexanediyl and the branched isomers thereof. Of particular utility in the invention are the β- or γ-cyclodextrin ethers or mixed ethers wherein the hydrogen atom of one or more cyclodextrin hydroxy groups is replaced by a hydroxyethyl, hydroxypropyl, dihydroxypropyl or hydroxyisobutyl group. The term mixed ether denotes β- or γ-cyclodextrin derivatives wherein at least two cyclodextrin hydroxy groups are etherified with different hydroxyalkyl groups such as, for example, hydroxypropyl and hydroxyethyl.

The average molar substitution (M.S.) is used as a measure of the average number of moles of alkoxy units per mole of anhydroglucose. In the cyclodextrin derivatives for use in the compositions according to the present invention the M.S. is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. The average molar substitution is conveniently determined by Fast Atom Bombardment Mass Spectroscopy (FAB-MS) in the negative mode.

The average substitution degree (D.S.) refers to the average number of substituted hydroxyls per anthydroglucose unit. In the cyclodextrin derivatives for use in the compositions according to the present invention the D.S. is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4.

More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin is less than 5% of the total cyclodextrin content and in particular is less than 1.5%.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents.

The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin.

Substituted cyclodextrins can be prepared according to procedures described in U.S. Pat. No. 3,459,731 and British Pat. Appl. No. 2,189,245 which are incorporated by reference for the processes for preparation. In general, unsubstituted cyclodextrins are reacted with an epoxide, preferably under superatmospheric pressure and at an elevated temperature, in the presence of an alkaline catalyst.

Other references describing cyclodextrins for use in the compositions according to the present invention, and which provide a guide for the preparation, purification and analysis of cyclodextrins include the following:
"Cyclodextrin Technology" by József Szejtli, Kluwer Academic Publishers (1988) in the chapter Cyclodextrins in Pharmaceuticals; "Cyclodextrin Chemistry" by M.L. Bender et at., Springer-Verlag, Berlin (1978); Advances in Carbohydrate Chemistry", Vol. 12 Ed. by M.L. Wolftom, Academic Press, New York (157) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p.343–361 (1981); A. P. Croft and R. A. Bartsch in Tetrahedron, 39, p. 1417–1474 (1983); Irie et al. Pharmaceutical Research,5,p. 713–716, (1988); Pitha et al. Int. J. Pharm. 29, 73, (1986); German Offenlegungsschrift DE 3118218; German Offenlegungsschrift DE 3317064; EP-A-94,157; EP-A-149,197; U.S. Pat. Nos. 4,659,696; and 4,383,992.

Particular attention should be paid to those references which describe the preparation and purification methods which provide cyclodextrin mixtures wherein the amount of unreacted cyclodextrin is less than 5% of the total cyclodextrin content.

The stability of erythropoietin in the aqueous solution increases with increasing concentrations of β- or γ-cyclodextrin until its level-off phase or maximal level. In the final compositions, the cyclodextrin will comprise about 2.5 to 20% by weight, in particular about 5 to 20%, more in particular 5 to 15%, for example about 10%, with the remainder being water, the active ingredient and any excipients.

In particular, stable pharmaceutical compositions may consist of water, cyclodextrin and erythropoietin only without the need of additional stabilizers such as, human serum albumin, bovine serum albumin, lecithin, methyl cellulose, polyethylene glycol, sulfur containing reducing agents, urea, amino acids and surfactants. There may be added a pH-adjusting agent e.g. hydrochloric acid, acetic acid, citric acid, sodium hydroxide, potassium hydroxide or a salt of any of these, in particular sodium citrate. The appropriate pH for formulating erythropoietin ranges from 6.5 to 7.4, in particular from 6.8 to 7.0.

For the preparation of an injectable it is appropriate to add an isotonizing agent, e.g. sodium chloride, potassium chloride, sorbitol.

Since trace amounts of heavy metal ions catalyse the degradation of erythropoietin it may further be appropriate to add a suitable complexing agent such as calcium chloride, citrate, EDTA and the like pharmaceutically acceptable metal ion complexing agents. For example, there may be added calcium chloride at a concentration of about 0.02–2 g/l.

The compositions according to the present invention have low toxicity, and are not irritating, thus permitting the manufacture of an injectable medicament which may safely be used in repeated dose regimes without the risk of immunogenic reactions. The preferred preparations are ready-for-use and are preferably administered subcutaneously or as a nasal spray or as eye drops. These preparations can be applied in an easy and simple manner and can therefore be self-administered, which permits therapy at home.

Further, the medicaments prepared according to this invention allow one to obtain a favourable pharmacokinetic profile of erythropoietin, affording a relatively constant plasma level during at least one day and hence provide a good physiological response, especially when given subcutaneously, or as nasal spray or eye drops.

The addition of an appropriate preservative to the preparations such as alcohols, for example, ethanol, 1,3-propanediol, benzylalcohol or derivatives thereof, phenyl ethyl alcohol, phenol or phenol derivatives such as butylparaben, methylparaben, m-cresol or chlorocresol; acids, for example, benzoic acid, sorbic acid, citric acid, sodium propionate, EDTA disodium; chlorhexidine; hexamidine diisetionate; hexetidine; optionally in combination with sodium bisulfite, or with propyleneglycol, or less preferably quaternary ammonium salts, metallic compounds such as zinc oxide, thiomersal and phenyl mercury salts, e.g. phenylmercuric acetate allows one to prepare safe multidose formulations of erythropoietin for parenteral and especially for local (e.g. nasal or ocular) administration. The preservative in said multidose formulations obviously is chosen so that it is compatible with the route of administration. Such a multidose formulation constitutes an economical and practicable advantage over the art-known single dose formulations.

The concentration of the pharmaceutically active agent in the preparations of this invention will of course depend on the type erythropoietin chosen, on its source, on its efficacy, on a comparison of its bioavailability by subcutaneous versus intravenous injection, and on the desired frequency of administration combined with the desired single dosage of the formulation. Preferably the concentration of erythropoietin in the preparation of the invention may be in the range of from about 100 to 50 000 international units (I.U.) per ml, particularly from about 500 to 20 000 I.U. per ml, more particularly from about 2 000 I.U. to 10 000 I.U. and especially about 4 000 I.U. (1 I.U. corresponds to 8.4 ng recombinant erythropoietin). In general it is contemplated that an effective amount would be from 1 to 200 I.U./kg bodyweight and more preferably from 2 to 100 I.U./kg bodyweight especially when the administration of erythropoietin is given subcutaneously. The effective amount will further depend on the species and size of the subject being treated, the particular condition and its severity and the route of administration. In any case the dose to be used should be one non-toxic to the host. As a subcutaneous dosage regimen in the treatment of patients with continuous ambulatory peritoneal dialysis (CAPD) the amount of erythropoietin administered should be such as to raise and maintain the haemoglobin levels at 10–12 g/dl.

The erythropoietin formulations described hereinbefore can conveniently be prepared by adding purified bulk erythropoietin to an aqueous solution of cyclodextrin and thoroughly mixing the resulting solution. Further pharmaceutically ingredients may be added, as desired, before, during or after the addition of the purified bulk erythropoietin. Said preparation is advantageously carried out at a low temperature, in particular below 10° C. and especially between 2° C. and 8°C.

An exemplary mode of preparing the erythropoietin preparations of this invention comprises dissolving or suspending erythropoietin in an aqueous solution of cyclodextrin comprising a buffer system, a pH adjusting agent, an isotonizing agent and/or the like. In the final composition, the molar ratio of cyclodextrin: erythropoietin can range from about 500 000:1 to 5000:1. Especially preferred in the final compositions is a molar ratio of hydroxypropyl-$\beta$-cyclodextrin: erythropoietin from about 200 000:1 to about 20 000:1, in particular from about 180 000:1 to about 30 000:1, more particularly from about 135 000:1 to about 90 000:1 or from about 85 000:1 to about 60 000:1. The weight-by-weight ratio of cyclodextrin to erythropoietin in the present compositions ranges from about 7 500:1 to about 700:1, in particular from about 6 000:1 to about 1 000:1, more particularly from about 4 500:1 to about 3 000:1 or from about 2 800:1 to about 2 000:1.

The aqueous preparations according to invention, and an excipient if required, may also be freeze-dried or spray-dried following art-known procedures to give a dehydrated composition which may be storm for a long period of time and dissolved before administration. In said freeze-dried or spray-dried formulations the molar ratio and the weight-to-weight ratio of cyclodextrin to erythropoietin may be the same as in the above-mentioned aqueous solutions. As it is convenient in a number of instances to reconstitute said freeze-dried or spray-dried formulation in an aqueous cyclodextrin solution, the molar ratio and the weight to weight ratio of cyclodextrin to erythropoietin may also be lower than in the above mentioned aqueous solutions. In such freeze-dried or spray-dried formulations the molar ratio of hydroxypropyl-$\beta$-cyclodextrin to erythropoietin can range from about 250 000:1 to about 2 000:1, especially from about 100 000:1 to about 5 000:1, in particular from about 50 000:1 to about 10 000:1.

The compositions according to the present invention have several surprising features. Thus, although it is already known that the cyclodextrins will form inclusion compounds with other compounds and will thereby increase the stability of these latter compounds, the formation of inclusion compounds has mainly been limited to situations in which the hydrofobic cavity can accommodate at least in part the guest compound. The present finding that also a macromolucule such as erythropoietin can be complexed and effectively stabilized with cyclodextrin derivatives is unexpected.

Whereas $\beta$-cyclodextrin and $\gamma$-cyclodextrin can prevent the adsorption of erythropoietin on the surface of the wall of the container, hydroxy-alkylated $\gamma$-cyclodextrin and in particular hydroxyalkylated $\beta$-cyclodextrin are more suitable for preventing substantial alterations of both the polypeptide and carbohydrate structure of the glycoprotein and as such increase the long term functional stability of the glycoprotein.

The liquid preparations according to the invention may be used in any dosage dispensing device adapted for parenteral e.g. subcutaneous administration or local administration e.g. nasal or ocular administration. The device should be constructed with a view to ascertaining optimum metering accuracy and compatibility of its constructive elements with the route of administration.

In a further aspect of the present invention there is provided a method for simultaneously stabilizing erythropoietin in an aqueous solution and preventing it from being adsorbed to surfaces by formulating said erythropoietin with an effective mount of a cyclodextrin derivative. The nature and effective amount of the cyclodextrin derivative for use in the present method in particular are those described in the erythropoietin-cyclodextrin compositions hereinbefore.

In still a further aspect of the invention there is provided a novel method of treating mammals suffering from anaemia by administering locally to said mammals an effective erythropoietic amount of the instant compositions. In particular said method comprises administering the present aqueous erythropoietin-cyclodextrin compositions to the nose as a nasal spray or the the eyes as eye drops.

Further details of practising this invention are furnished by way of the following examples which, however, should not be construed so as to impose any limitation to the scope of this invention.

A. Composition examples

Example 1

Injectable solution

| a) Erythropoietin 4000 I.U./ml | |
|---|---|
| Human recombinant erythropoietin (r-HuEPO) | 4000 U |
| Sodium chloride | 3.59 mg |
| Sodium citrate 2 aq | 5.8 mg |
| Citric acid 1 aq | 62 µg |
| Hydroxypropyl-β-cyclodextrin (MS = 0.4) | 100 mg |
| Hydrochloric acid (1 N) or | q.s. ad pH 6.9 |
| Sodium hydroxide (1 N) | |
| Water | q.s. ad 1 ml |

Method of preparation 18 l cold pyrogen free water was sterilized by filtration. Thereto were added with stirring 2 kg hydroxypropyl-β-cyclodextrin (M.S.=0.4), 116 g sodium citrate.2aq, 1.24 g citric acid.laq and 71.8 g sodium chloride. The solution was cooled to 25° C. and the pH was adjusted to pH 6.9 by addition of NaOH (1N) or HCl (1N). The solution was stirred until homogenous and cooled at 2° C. to 8° C.

500 ml r-HuEPO purified bulk (160 000 I.U./ml) stored at −70° C. to −80° C. was liquified by immersion m a water bath at 20° C. The thawed solution was added to the citric acid buffer solution and stirred for 5 minutes at a temperature below 8° C. This solution was diluted with cold pyrogen free water to a final volume of 20 l and was sterilized by filtration under sterile nitrogen. The final solution was filled into sterile 1 ml containers.

The following formulations were prepared similarly employing suitable amounts of the ingredients in order to obtain a final solution of the required composition.

| b) Erythropoietin 2000 I.U./ml | |
|---|---|
| Human recombinant erythropoietin (r-HuEPO) | 2000 U |
| Sodium chloride | 5.84 mg |
| Sodium citrate 2 aq | 5.8 mg |
| Citric acid 1 aq | 62 µg |
| Hydroxypropyl-β-cyclodextrin (MS = 0.4) | 50 mg |
| Hydrochloric acid (1 N) or | q.s. ad pH 6.9 |
| Sodium hydroxide (1 N) | |
| Water | q.s. ad 1 ml |

| c) Erythropoietin 10 000 I.U./ml | |
|---|---|
| Human recombinant erythropoietin (r-HuEPO) | 10 000 U |
| Sodium citrate 2 aq | 5.8 mg |
| Citric acid 1 aq | 62 µg |
| Hydroxypropyl-β-cyclodextrin (MS = 0.4) | 200 mg |
| Hydrochloric acid (1 N) or | q.s. ad pH 6.9 |
| Sodium hydroxide (1 N) | |
| Water | q.s. ad 1 ml |

Example 2

Eye drops

| | |
|---|---|
| Human recombinant erythropoietin (r-HuEPO) | 4000 U |
| Sodium chloride | 3.59 mg |
| Sodium citrate 2 aq | 5.8 mg |
| citric acid 1 aq | 62 µg |
| Phenylmercuric acetate | 0.02 mg |
| Hydroxypropyl-β-cyclodextrin (MS = 0.4) | 100 mg |
| Hydrochloric acid (1 N) or | q.s. ad pH 6.9 |
| Sodium hydroxide (1 N) | |
| Water | q.s. ad 1 ml |

Example 3

Nasal spray

| | |
|---|---|
| Human recombinant erythropoietin (r-HuEPO) | 4000 U |
| sodium chloride | 3.59 mg |
| Sodium citrate 2 aq | 5.8 mg |
| Citric acid 1 aq | 62 µg |
| Thiomersal | 0.2 mg |
| Hydroxypropyl-β-cyclodextrin (MS = 0.4) | 100 mg |
| Hydrochloric acid (1 N) or | q.s. ad pH 6.9 |
| Sodium hydroxide (1 N) | |
| Water | q.s ad 1 ml |

B. Biological examples

Example 4

Stabilizing effect of various cyclodextrins on EPO

The structural integrity of erythropoietin with different stabilizers was investigated using a combination of ion exchange chromatography and polyacrylamide gel electrophoresis. The stabilizing effect of different cyclodextrin derivatives was compared with human albumin. The EPO (Erythropoietin) solutions used according to the present invention were prepared as follows: 1 mg of EPO (Amgen) was diluted into 2.6 ml citric acid buffer (sodium citrate.2H$_2$O: 5.80 g, citric acid.H$_2$O: 0.0623 g and sodium chloride: 5.84 g into 1000 ml water and purified by reverse osmosis and ultrafiltration. The buffer was filtered through a 0.22 µm filter). This stock solution of EPO was diluted into a solution of hydroxypropyl-β-cyclodextrin (MS=0.4) or hydroxypropyl-γ-cyclodextrin (MS=0.4) in the citric acid buffer defined hereinabove. The resulting final concentration of the cyclodextrins was 5 and 20%, the final EPO concentration was 33 µg/ml, equivalent to 4000 U/ml. For the comparison with human serum albumin (HSA) as a stabilizer, readily formulated EPO obtained from Cilag (lot No 88Z008) was used. The composition of this material was: sodium citrate.2H$_2$O:5.8 mg, citric acid: 0.057 mg, sodium chloride: 5.84 mg, human albumin: 2.5 mg and 0.0336 mg erythropoietin into 1 ml water. Control solution consists of 0.0336 mg erythropoietin in 1 ml water. The different solutions were kept in glass containers at 57° C., in a temperature-controlled waterbath. The stabilizing effect of cyclodextrins on EPO was investigated by ion exchange chromatography by comparing the purified EPO peak height before incubation with the peak height after 10 days and after 3 weeks at 57°C. The chromatographic method used was as follows:

Instrument :FPLC (Pharmacia, Uppsala, Sweden)

Detection system :UV adsorption at 280 nm
Column :Mono Q (Pharmacia, Uppsala, Sweden)

EPO containing fractions of 500 μl were applied to the Mono Q column (0.5×5 cm) at room temperature. Buffer A was 20 mM Tris (pH 8.0); buffer B was 20 mM Tris (pH 8.0) containing 1M NaCl. The flow rate was 1 ml/min. A stepped salt gradient was used. EPO was eluted after about 16 minutes, (the corresponding NaCl concentration was 16 mM).

This technique showed a complete separation of EPO from either serum albumin or cyclodextrin as verified by electrophoresis. The peak height of the EPO fraction was measured. The purity and homogeneity of the protein fractions eluted at 16 mM NaCl were controlled by means of polyacrylamide gel electrophoresis. The electrophoresis was done as follows.

An aliquot of the EPO containing fraction was reduced by mixing with a sample buffer (0.167M Tris, 33% glycerol, 3.3% sodium dodecyl sulphate, 4% dithiothreitol; 0.005% bromophenol blue pH 6.8) and incubated at 100° C. for 5 minutes. 15 μl of the sample was applied to the lane of a 10% sodium dodecyl sulphate polyacrylamide gel. The electrophoresis was performed using an electrophoresis buffer (0.38M glycine/Tris pH 8.3, 0.1% sodium dodecyl sulphate) for 90 minutes at 150 V according to the method described in Laemmli, U., (1970) Nature (London) 227, 680–685.

The gel was then silver stained using the method described in Morrissey J.H., (1981) Anal. Biochem. 117, 307–310. The electrophoretic experiment clearly showed that the EPO fraction was homogeneous when using cyclodextrin derivatives as stabilizer. The EPO fraction using human albumin as stabilizer showed the presence of proteins with higher molecular weight and the percentage EPO was low in comparison with the degradation products present.

The degradation products originated most likely from the albumin. This may explain why the peak height of the EPO fraction with human albumin as stabilizer was higher after 3 weeks than at the beginning. This also implies that the ion exchange chromatographic technique must be used in combination with the electrophoretic technique in order to evaluate the stabilization of the EPO.

Table 1 summarizes the results of the experiment.

TABLE 1

| Protection used | EPO Peak height (cm) before incubation | EPO Peak height (cm) after 10 days | Remaining EPO (%) | EPO Peak height (cm) after 20 days | Remaining EPO (%) |
|---|---|---|---|---|---|
| Control | 11.9 | 6.0 | 50% | 2.9 | 24% |
| HSA 0.25% | 10.6 | 6.4/5.1(*) | 48% | 10.7/3.2(*) | 30% |
| HP-β-CD 5% | 11.5 | 5.4 | 47% | 6.3 | 55% |
| HP-β-CD 20% | 11.5 | 13.4 | 100% | 7.1 | 62% |
| HP-γ-CD 5% | 11.2 | 5.1 | 46% | 3.2 | 29% |
| HP-γ-CD 20% | 12.5 | 9.7 | 78% | 4.5 | 36% |

(*)The EPO peak heights of the human serum albumin-containing formulation before and after correction based on the electrophoretic assessment of the EPO content.

Example 5

Stabilizing effects of various cyclodextrin concentrations on EPO

In a second experiment the stabilizing effect of different hydroxypropyl-β-cyclodextrin concentrations was investigated using the same methodology. The electrophoretic results showed that, when hydroxypropyl-β-cyclodextrin was used as stabilizer, the fraction eluted at 16 mM NaCl consisted of pure EPO, no degradation products could be demonstrated. The EPO fraction using human serum album as stabilizer again showed the presence of degradation products of higher molecular weight. The results are summarized in table 2.

TABLE 2

| Protection used | EPO Peak height (cm) before incubation | EPO Peak height (cm) after 7 days | Remaining EPO (%) | EPO Peak height (cm) after 18 days | Remaining EPO (%) |
|---|---|---|---|---|---|
| Control | 11.1 | 3.3 | 30% | 4.2 | 38% |
| HSA | 10.5 | 9.5/3.8(*) | 36% | 9.0/0.5(*) | 5% |
| HP-β-CD 5% | 12.8 | 6.4 | 50% | 5.5 | 43% |
| HP-β-CD 10% | 12.1 | 6.9 | 57% | 6.8 | 56% |
| HP-β-CD 15% | 12.7 | 6.8 | 54% | 6.4 | 50% |
| HP-β-CD 20% | 11.4 | 7.0 | 61% | 4.8 | 42% |

(*)The EPO peak heights of the human serum albumin-containing formulation before and after correction based on the electrophoretic assessment of the EPO content.

To summarize these experiments we can conclude that cyclodextrin derivatives protect EPO from degradation. The protection obtained with cyclodextrins was better than the one obtained with human serum albumin, at least in the experimental conditions used.

Example 6

Adsorption of EPO on plastic material in the presence of cyclodextrin

The EPO solution used in this study was prepared as follows:

1 mg of EPO (Amgen) was diluted into 2.6 ml citric acid buffer (sodium citrate.2H$_2$O: 5.80 g, citric acid.-H$_2$O: 0.0623 g and sodium chloride: 5.84 g into 1000 ml water purified by reverse osmosis and ultrafiltration. The buffer was filtered through a 0.22 μm filter). This stock solution of EPO was diluted into a solution of hydroxypropyl-β-cyclodextrin in the above defined citric acid buffer. The final concentration of hydroxypropyl-β-cyclodextrin was 10 or 20%. The final concentration of EPO was 33 μg/ml. In case human albumin was used as carrier, the EPO Cilag lot No 89I21/443 was used as a reference.

1 ml of the various EPO solutions were injected into an infuse set (Universal set 315 C0339 from Travenol) and left overnight at 4° C. After recovery the chromatographic and electrophoretic protocols as described above were performed. The peak height of the protein fraction eluted at 16 mM NaCl was measured.

Table 3 summarizes the results. The figures are the results obtained in two different experiments.

TABLE 3

| Protection used | EPO peak height (cm) before adsorption | | EPO peak height (cm) after adsorption | | Unadsorbed EPO(%) | |
|---|---|---|---|---|---|---|
| Experiment | 1 | 2 | 1 | 2 | 1 | 2 |
| Control | 9.6 | 9.2 | 3.5 | 4.0 | 36.5% | 43.5% |
| HSA | 9.8 | 5.7 | 8.4 | 5.3 | 85.7% | 93.0% |
| HP-$\beta$-CD 10% | 11.4 | 13.4 | 11.3 | 10.2 | 99.1% | 76.1% |
| HP-$\beta$-CD 20% | 12.9 | 10.4 | 12.4 | 11.2 | 96.1% | 107.6% |

For all samples tested, the electrophoretic results showed that the fraction eluted at 16 mM NaCl consisted of pure EPO, no degradation products could be demonstrated.

From these experiments we can conclude that hydroxypropyl-$\beta$-cyclodextrin prevents the adsorption of EPO on the plastic material used in infuse sets as well as human serum albumin does.

Example 7

Erythropoietin Mouse Bioassay

The exhypoxic polycythemic mouse bioassay is used to verify the biological activity of r-HuEPO. In this assay, mice are acclimated to reduced atmospheric pressure (approximately 0.4 atm.) for two weeks to induce red blood cell formation in response to natural physiological erythropoietin production. When the mice are returned to normal atmospheric conditions, the high oxygen-carrying capacity of the increased circulating red cells suppresses further endogenous erythropoietin production. Under these conditions, the animal will respond with further induction of red cell formation to exogenously applied erythropoietin in a dose-dependent manner. Quantitation of new red cell production is accomplished by measuring uptake of radioactive iron ($^{59}$Fe). Dose-response curves obtained with sample r-HuEPO (Human recombinant erythropoietin) test cyclodextrin preparations are compared to that of the r-HuEPO standard to determine sample activity.

Example 8

Comparative study

Bioavailability of erythropoietin after subcutaneous administration of erythropoietin in a hydroxypropyl-$\beta$-cyclodextrin formulation in comparison with formulations using human serum albumin in healthy volunteers was assessed in the following study.

Six healthy male volunteers with ages ranging between 30 and 40 (median 32) years, body weights between 69 and 80 (median 75) kg were administered subcutaneously in the upper arm 1 ml of an EPO solution (4000 I.U./ml) according to a randomized crossover design. A four-week interval occured between the two tests. The two formulations of EPO were A: a marketed solution with 4 000 I.U./ml

| (Eprex ®, Cilag; Lot No. 89128/385) | | |
|---|---|---|
| r-HuEPO | 4 000 | I.U. |
| Human serum albumine | 2.5 | mg |
| Sodium chloride | 5.84 | mg |
| Sodium citrate.2 H$_2$O | 5.8 | mg |
| Citric acid | 0.057 | mg |
| Water for injection ad | 1 | ml |
| B: a solution with 4 000 I.U./ml containing 10% of hydroxypropyl-$\beta$-cyclodextrin | | |
| r-HuEPO | 4 000 | I.U. |
| Sodium chloride | 3.59 | mg |
| Sodium citrate.2 H$_2$O | 5.8 | mg |
| Citric acid | 0.057 | mg |
| Hydroxypropyl-$\beta$-cyclodextrin (M.S. = 0.4) | 100 | mg |
| Water for injection ad | 1 | ml |

Venous blood samples (4 ml) for the determination of EPO were taken immediately before and 2, 4, 6, 8, 10, 12, 24, 32, 48, 56, 72 and 96 h after administration and were allowed to clot at room temperature. During the first 12 hours samples were taken from the opposite arm. Separated serum was stored at −20° C. until assayed.

Plasma concentrations of EPO were measured by an enzyme immunoassay (EIA) with a detection limit of 5 mU/ml up to 96 hours after administration according to the procedures outlined in Clinigen Erythropoietin EIA Kit, 96 tests (No. ABC06096), User's manual.

The following pharmacokinetic parameters of EPO were determined.

peak plasma concentration ($C_{max}$:mU/ml)
time to the peak plasma concentration ($T_{max}$:h)
area under the plasma concentration-time curve ($AUC_{0-96h}$:mU.h/ml)
relative bioavailability of the hydroxypropyl-$\beta$-cyclodextrin formulation compared to the marked formulation, i.e. $AUC_{0-96h}$ ratio × 100 ($F_{rel}$:%)

Differences of the above parameter values between the two formulations had no statistical significance.

| Comparative bioavailability of EPO after S.C. administration | | |
|---|---|---|
| Parameter | A (Eprex ®; Cilag) | B (10% HP-$\beta$-CD) |
| $T_{max}$:h | 16.3 ± 8.5 | 19.7 ± 11.0 |
| $C_{max}$:mU.h/ml | 33.4 ± 7.5 | 30.8 ± 9.9 |
| $AUC_{0-96h}$:mU.h/ml | 1864 ± 548 | 1753 ± 428 |
| $F_{rel}$, % | | 96.4 ± 14.5 |

Erythropoietin was slowly absorbed after subcutaneous administration of both the marketed formulation (Eprex ®) and the newly developed hydroxypropyl-$\beta$-cyclodextrin formulation. From about 10 to 24 hours after administration of both formulations, near-peak plasma levels in the order of 30 mU/ml were observed. The relative bioavailability of the hydroxypropyl-$\beta$-cyclodextrin formulation to the marketed formulation was 96%. One can conclude that both formulations are bioequivalent in rate and extent of absorption.

Irritation at the site of injection was scored before and 2, 4, and 24 hours after each administration. No oedema, erythema, itching or pain was reported in any of the volunteers at any time during the whole study. Both formulations are therefore equally well tolerated.

No clinically important changes were observed in haematology and serum biochemistry. Nor did subcutaneous administration of EPO influence blood pressure or heart rate.

We claim:

1. A method for simultaneously stabilizing erythropoietin in an aqueous solution and preventing it from being adsorbed to surfaces by formulating said erythropoietin with an effective amount of β- or γ-cyclodextrin wherein one or more of the hydroxy moieties of the anhydroglucose units of the β- or γ-cyclodextrin have been replaced by a radical of the formula:

$$-O-[Alk-O-]_n-H \quad (I)$$

wherein Alk represents a member selected from the group consisting of straight or branched chain $C_{1-6}$alkanediyl radical and straight or branched chain $C_{1-6}$alkanediyl radicals having one hydrogen atom of said $C_{1-6}$alkanediyl replaced by a hydroxy group; and "n" represents a number having a value within the range of from 1 to 5, wherein the average number of moles of -Alk-O— units per anhydroglucose moieties in said β- or γ-cyclodextrin is within the range of from 0.3 to 3, and wherein the weight ratio of β- or γ-cyclodextrin to erythropoietin in said composition is within the range of from about 7,500:1 to about 700:1.

2. A method according to claim 1 wherein the β- or γ-cyclodextrin is a β-or γ-cyclodextrin ether or mixed ether wherein the hydrogen of one or more β- or γ-cyclodextrin hydroxy groups are replaced by a hydroxyethyl, hydroxypropyl or hydroxyisobutyl group.

3. A method according to claim 1 Wherein the average molar substitution (M.S.) is in the range of 0.3 to 0.8.

4. A method according to claim 1 wherein the weight-by-weight ratio of β- or γ-cyclodextrin to erythropoietin is within the range of from about 6,000:1 to about 1,000:1.

* * * * *

UNITED STATES PATENT AND TRADEMARK OFFICE
CERTIFICATE OF CORRECTION

PATENT NO. : 5,376,632
DATED : Dec. 27, 1994
INVENTOR(S) : Frank J. Konings, et al It is certified that error appears in the above-indentified patent and that said Letters Patent is hereby corrected as shown below:

On title page, add the following:

--[30] Foreign Priority Application Data January 29, 1990 [GB] Great Britain...90.01.987.8 January 25, 1991 [PCT]... PCT/EP 91/00173 ...

Signed and Sealed this

Nineteenth Day of September, 1995

Attest:

BRUCE LEHMAN

*Attesting Officer*  *Commissioner of Patents and Trademarks*